US00PP35847P2

(12) United States Plant Patent
Clark

(10) Patent No.: US PP35,847 P2
(45) Date of Patent: May 28, 2024

(54) ***COLEUS* PLANT NAMED 'UF22-140-3'**

(50) Latin Name: *Coleus scutellarioides*
Varietal Denomination: UF22-140-3

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/445,295

(22) Filed: Jun. 20, 2023

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469
See application file for complete search history.

(56) References Cited

U.S. PATENT DOCUMENTS

PP34,066 P2 3/2022 Clark

*Primary Examiner* — Susan McCormick Ewoldt
(74) *Attorney, Agent, or Firm* — Koenig IP Works, PLLC; Katherine Koenig

(57) ABSTRACT

'UF22-140-3' is a new *Coleus* plant, selected for having a combination of desirable traits that make it well-suited for use as an annual plant in the summer landscape. 'UF22-140-3' was selected for its consistent foliage color patterning, and also for its fast growth rate and vigor in the greenhouse and landscape. 'UF22-140-3' has ruffled, highly lobed leaves that are predominantly colored greyish purple with consistent purplish red centers and midveins and yellow green leaf margins. 'UF22-140-3' maintains these contrasting colors and patterns in both sun and shade. 'UF22-140-3' is upright in habit, but it is highly branched and spreading in form, growing slightly wider than it does tall.

3 Drawing Sheets

Genus and species: *Coleus scutellarioides*.
Cultivar denomination: 'UF22-140-3'.

BACKGROUND OF THE NEW CULTIVAR

The invention relates to a new and distinct cultivar of *Coleus* plant named 'UF22-140-3'. The new cultivar 'UF22-140-3' originated from an open pollination conducted in May-November 2021 in Citra, Florida, between the female *Coleus* plant 'UF21-61-12' (unpatented) and an unknown male *Coleus* plant. A single seedling was chosen in May 2022 for further asexual propagation in Gainesville, Florida.

The new cultivar 'UF22-140-3' has been reproduced asexually for over 11 months through vegetative meristem tip cuttings and has been found to retain its distinctive characteristics through successive asexual propagations. 'UF22-140-3' was first propagated asexually by vegetative meristem tip cuttings in May 2022 in Gainesville, Florida, and has remained true-to-type since that time.

Plant Breeder's Rights for the new cultivar 'UF22-140-3' have not been applied for, and 'UF22-140-3' has not been made publicly available more than one year prior to the filing date of this application.

SUMMARY OF THE INVENTION

The new cultivar 'UF22-140-3' has not been observed under all possible environmental conditions. The phenotype of the new cultivar may vary with variations in environment and cultural practices such as temperature, light intensity, fertilization, irrigation, and application of plant growth regulators without any change in genotype.

The new cultivar 'UF22-140-3' was selected for its large leaves and consistent foliage color patterning. It has a vigorous and fast growth rate in the greenhouse and landscape. 'UF22-140-3' has foliage that is predominantly colored greyish purple with consistent yellow green leaf margins and purplish red centers around the midveins. Normally this color combination changes in either full sun (predominantly dark brick red) or full shade (predominantly brownish red), with the consistent loss of the distinctive purplish red midveins. 'UF22-140-3' is exceptional because it maintains consistent color patterning in both sun and shade.

The following are the most outstanding and distinguishing characteristics of 'UF22-140-3' when grown under normal horticultural practices in Gainesville, Florida: (1) 'UF22-140-3' has the combination of vigorous, upright habit and spreading growth form, excellent heat tolerance, and consistent multi-colored leaves that are significantly different than other *Coleus* plants; (2) it has superior stability in foliage color in both sun and shade conditions, and it has a vigorous growth habit with excellent lateral branching, making it suitable for propagators and producers; and (3) 'UF22-140-3' has been observed to have long-season performance in landscape trials in Gainesville, Florida.

When compared to the female parent 'UF21-61-12', 'UF22-140-3' has large, ruffled, and highly lobed leaves that are as long as they are wide, whereas 'UF21-61-12' has large, highly lobed leaves that are much longer than they are wide. Additionally, 'UF22-140-3' has leaves that are predominantly colored greyish purple with purplish red centers and midveins and distinct yellow green margins, whereas 'UF21-61-12' has leaves that are predominantly colored crimson red with chartreuse margins. Finally, 'UF22-140-3' has a vigorous and upright habit and spreading form, whereas 'UF21-61-12' is less vigorous, with a more prostrate habit with more lateral branching and a more spreading form.

DESCRIPTION OF THE FIGURES

This new *Coleus* cultivar 'UF22-140-3' is illustrated by the accompanying photographs, which show the plant's form and foliage. The colors shown are as true as can be reasonably obtained by conventional photographic procedures.

FIG. 2 shows the growth habit, form, and foliage of the new *Coleus* cultivar; and FIG. 3 shows a close-up view of the foliage of the new *Coleus* cultivar.

DETAILED BOTANICAL DESCRIPTION OF THE CULTIVAR

Figure 1:
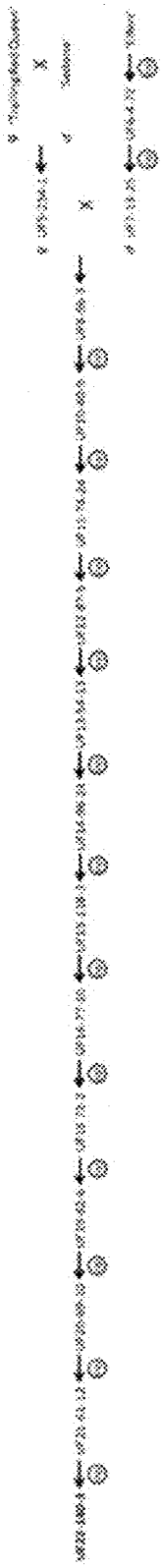
FIG. 1 shows the pedigree of the new *Coleus* cultivar 'UF22-140-3' as is shown and described herein.
Figure 2:
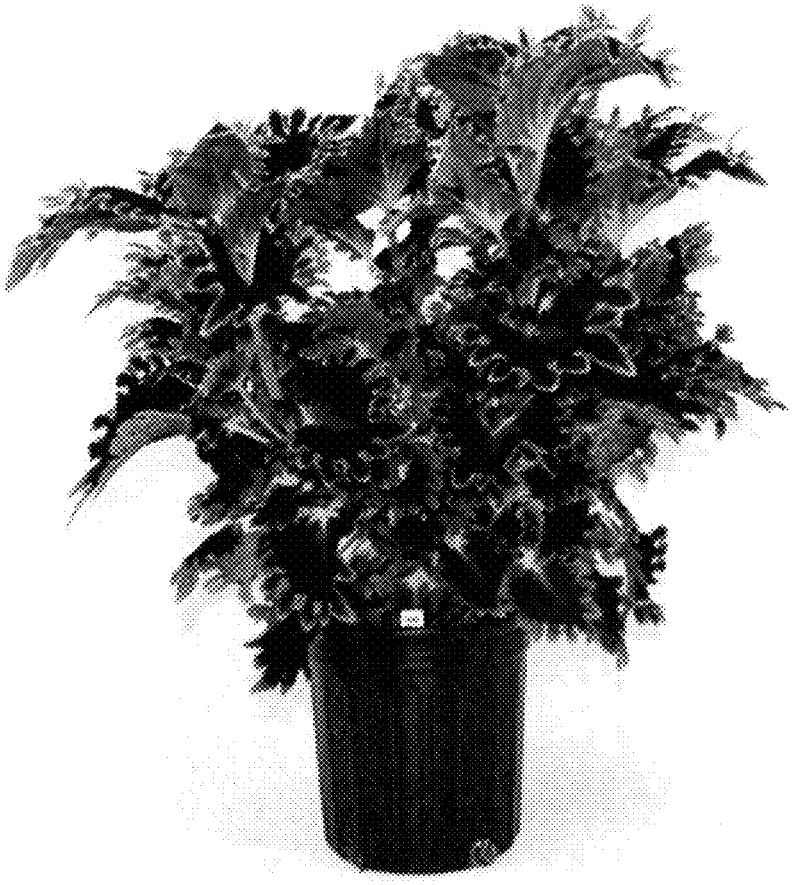
FIGS. 2 and 3 were taken from plants grown eleven weeks from unrooted cuttings in September-December 2022 in a glass-covered greenhouse in Gainesville, Florida.
Figure 3:
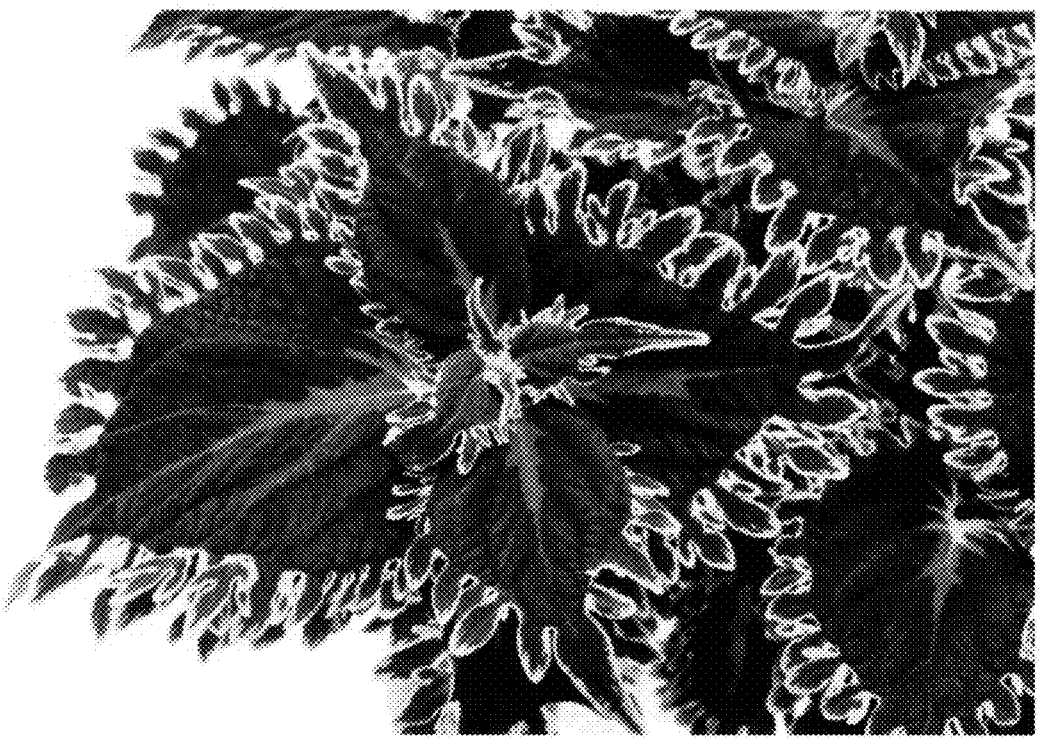

Foliage color was determined under full sun conditions in the middle of the day in a glass-covered greenhouse. Color references are to the RHS Colour Chart of The Royal Horticultural Society of London (RHS), 2007 5th Edition. *Coleus* leaves are rarely one solid color but encompass hues, shades and tints, and color patterns differ from one genotype to another due to varying levels of variegation. The following detailed description of 'UF22-140-3' was obtained using eleven-week-old plants grown from unrooted cuttings in September-December 2022 in a glass-covered greenhouse in Gainesville, Florida. The plants were propagated in mist for ten days after cuttings were stuck, pinched, then grown in one-gallon pots for approximately nine and a half additional weeks.

Botanical description:

Botanical classification:

*Family.*—Lamiaceae.

*Botanical name.*—*Coleus scutellarioides.*

*Common name.*—*Coleus.*

*Cultivar name.*—'UF22-140-3'.

Parentage:

*Female or seed parent.*—'UF21-61-12'.

*Male or pollen parent.*—Unknown.

Plant description:

*Form.*—Spreading.

*Habit.*—Upright.

*Height* (*from top of soil*).—30-35 cm.

*Width* (*horizontal plant diameter*).—50-55 cm.

Propagation:

*Type cuttings.*—Vegetative meristems having at least 1 node.

*Time to initiate roots.*—3-4 days.

*Time to produce a rooted cutting.*—7-10 days.

*Root habit.*—Fibrous.

*Root description.*—Callus forms in 2-3 days, roots initiate in 3-4 days and become a highly branched cutting in 7-10 days.

Branches:

*Quantity per plant.*—Approximately 6-7.

*Branch color.*—RHS 143C (yellow green).

*Texture.*—Smooth.

*Pubescence.*—Not present.

*Stem description.*—Square-shaped stem.

*Branch diameter.*—0.8-0.9 cm at the base of a 30-cm-long branch.

*Branch length.*—25-30 cm.

*Internode length.*—4 cm measured at mid-branch.

*Anthocyanin.*—Not present.

Leaves:

*Quantity of leaves per branch.*—18-20.

*Arrangement.*—Opposite.

*Fragrance.*—Not fragrant.

*Shape.*—Ovate.

*Length.*—12-13 cm.

*Width.*—12-13 cm.

*Apex.*—Broadly acute.

*Base.*—Attenuate.

*Margin.*—Laciniate.

*Marghin, depth of incision of lobes.*—2-3 cm.

*Leaf texture.*—Adaxial (top): Pulverulent. Abaxial (bottom): Smooth.

*Venation color.*—Upper surface: RHS N186A (purplish grey). Lower surface: RHS 145C (light yellow green).

*Venation pattern* (*both upper and lower surfaces*).—Reticulate.

*Color, immature leaf.*—Upper surface: Major color: RHS N77A (greyish purple). Center and midveins: RHS 60A (deep red). Margins: RHS 144A (yellow green). Base: RHS 150B (yellow green). Lower surface: Major color: RHS 138A (yellowish green. Center and midveins: RHS 187C (dark red). Base: RHS 150C (yellow green).

*Color, mature leaf.*—Upper surface: Major color: RHS N77A (greyish purple). Center and midveins: RHS 61A (purplish red). Margins: RHS 144A (yellow green). Base: RHS 145C (yellow green). Lower surface: Major color: RHS 138A (yellowish green). Center and midveins: RHS N186C (greyish red). Base: RHS 157A (pale yellow green).

*Petiole length.*—4 cm.

*Petiole diameter.*—0.3-0.4 cm.

*Petiole color.*—RHS 145A (yellow green).

*Petiole texture.*—Smooth, no pubescence.

Flowers and seeds: Flowers and seeds have not been observed to date during formal trials in Gainesville, Florida.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Florida have been long-tailed or citrus mealybugs (*Pseudococcus* spp.), which occur on older stock plant material held in the greenhouse for over 3-4 months. Impatiens Necrotic Spot Virus (Bunyaviridae) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

Winter hardiness: Not winter hardy, grown as a summer annual in USDA zones below 7.

Heat and drought tolerance: Heat tolerance when grown in moist and well-drained soil. Not drought tolerant.

Comparison with known cultivars: When compared to the *Coleus* cultivar 'UF18-62-10' (U.S. Plant Pat. No. 34,066, commercial name Vulcan), the new *Coleus* cultivar 'UF22-140-3' has a broad center leaf coloration of purplish red surrounded by greyish purple on the upper surface of mature leaves, whereas 'UF18-62-10' has a leaf coloration of mostly dark red with a narrow center leaf coloration of purplish red along the mid vein on the upper surface of mature leaves.

What is claimed is:

1. A new and distinct *Coleus scutellarioides* plant named 'UF22-140-3' as shown and described herein.

* * * * *